United States Patent
Brown et al.

[19]

[11] Patent Number: 6,127,310
[45] Date of Patent: *Oct. 3, 2000

[54] PALLADIUM CONTAINING HYDROGENATION CATALYSTS

[75] Inventors: Scott H. Brown; Tin-Tack Peter Cheung, both of Bartlesville, Okla.

[73] Assignee: Phillips Petroleum Company, Bartlesville, Okla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/808,047

[22] Filed: Feb. 27, 1997

[51] Int. Cl.[7] .................................................... B01J 23/44
[52] U.S. Cl. .......................... 502/339; 502/344; 502/347; 502/348; 502/325; 502/326; 502/327; 502/328; 502/329; 502/330; 502/332; 502/333
[58] Field of Search ................................... 502/344, 347, 502/348, 325, 326, 327, 328, 329, 330, 332, 333, 339

[56] References Cited

U.S. PATENT DOCUMENTS

| | | | |
|---|---|---|---|
| 2,681,938 | 6/1954 | Lindlar | 260/311 |
| 3,477,962 | 11/1969 | Kardys | 252/412 |
| 3,651,167 | 3/1972 | di Rosset | 260/681.5 |
| 3,878,089 | 4/1975 | Wilhelm | 208/139 |
| 3,948,808 | 4/1976 | Box, Jr. et al. | 252/462 |
| 3,957,688 | 5/1976 | Farha, Jr. et al. | 252/455 R |
| 4,191,846 | 3/1980 | Farha, Jr. et al. | 585/440 |
| 4,227,025 | 10/1980 | Montgomery | 585/259 |
| 4,321,401 | 3/1982 | Yoshida et al. | 560/244 |
| 4,337,329 | 6/1982 | Kubo et al. | 525/339 |
| 4,484,015 | 11/1984 | Johnson et al. | 585/262 |
| 4,504,593 | 3/1985 | Trinh Dinh et al. | 502/154 |
| 4,906,800 | 3/1990 | Henry et al. | 585/260 |
| 5,057,206 | 10/1991 | Engel et al. | 208/143 |
| 5,105,032 | 4/1992 | Holbrook et al. | 570/101 |
| 5,283,379 | 2/1994 | Saiki et al. | 570/156 |
| 5,356,851 | 10/1994 | Sarrazin et al. | 502/185 |
| 5,413,984 | 5/1995 | Marecot et al. | 502/333 |
| 5,475,173 | 12/1995 | Cheung et al. | 585/259 |
| 5,489,565 | 2/1996 | Cheung et al. | 502/325 |
| 5,498,806 | 3/1996 | Ichikawa et al. | 570/156 |
| 5,527,946 | 6/1996 | Flick et al. | 558/459 |
| 5,583,274 | 12/1996 | Cheung et al. | 585/261 |
| 5,585,318 | 12/1996 | Johnson et al. | 502/330 |
| 5,587,348 | 12/1996 | Brown et al. | 502/230 |
| 5,648,576 | 7/1997 | Nyguyen Than et al. | 585/260 |
| 5,698,752 | 12/1997 | Brown et al. | 585/260 |
| 5,750,806 | 5/1998 | Brocker et al. | 568/909.5 |
| 5,866,734 | 2/1999 | Flick et al. | 585/260 |
| 5,866,746 | 2/1999 | Didillion et al. | 585/661 |

FOREIGN PATENT DOCUMENTS

| | | |
|---|---|---|
| 0398466 | 11/1990 | European Pat. Off. . |
| 2720946 | 12/1995 | France . |
| 1018661 | 1/1966 | United Kingdom . |

OTHER PUBLICATIONS

Engelhard De Meern "Hydrogenation and/or dehydrogenation catalysts–contg. hydrogenation component and metal oxide as separate particles"—abstract of EP 398446, Nov. 1990.

Author:Ohnishi et al., Abstract of Selective hydrodechlorination of CFC–113 on Bi– and TI–modified palladium catalysts, 1994—no month.

*Primary Examiner*—Marian C. Knode
*Assistant Examiner*—Nadine Preisch
*Attorney, Agent, or Firm*—Richmond, Hitchcock, Fish & Dollar

[57] ABSTRACT

A composition and a process for using the composition in a selective hydrogenation of a highly unsaturated hydrocarbon such as, for example, an alkyne or diolefin, to a less unsaturated hydrocarbon such as, for example, an alkene or a monoolefin, are disclosed. The composition comprising palladium, a selectivity enhancer and an inorganic support wherein the palladium and selectivity enhancer are each present in a sufficient amount to effect the selective hydrogenation of a highly unsaturated hydrocarbon. Optionally, the composition can comprise silver. Also optionally, the palladium is present as skin distributed on the surface of the support. The composition can further comprise an alkali metal-containing compound such as, for example, potassium fluoride.

12 Claims, No Drawings

PALLADIUM CONTAINING HYDROGENATION CATALYSTS

FIELD OF THE INVENTION

This invention relates to a composition and a process useful for catalytically hydrogenating an unsaturated hydrocarbon compound.

BACKGROUND OF THE INVENTION

It is well known to one skilled in the art that an unsaturated hydrocarbon compound can be produced by a thermal cracking process. For example, a fluid stream containing a saturated hydrocarbon such as, for example, ethane, propane, butane, pentane, naphtha, or combinations of any two or more thereof can be fed into a thermal (or pyrolytic) cracking furnace. Within the furnace, the saturated hydrocarbon is converted to an unsaturated hydrocarbon compound such as, for example, ethylene and propylene. Unsaturated hydrocarbons are an important class of chemicals that find a variety of industrial uses. For example, ethylene can be used as a monomer or comonomer for producing a polyolefin. Other uses of unsaturated hydrocarbons are well known to one skilled in the art.

However, an unsaturated hydrocarbon produced by a thermal cracking process generally contains an appreciable amount of highly unsaturated hydrocarbons such as the less desirable alkyne(s), diolefin(s), polyene(s), or combinations of two or more thereof. For example, ethylene produced by thermal cracking of ethane is generally contaminated with some acetylene which must be selectively hydrogenated to ethylene, but not to ethane, in a hydrogenation reaction. Similarly, propylene produced by thermal cracking of a saturated hydrocarbon is generally contaminated with propyne and propadiene which must be selectively hydrogenated to propylene, but not propane. In a thermal cracking process for producing a butene, butynes and butadienes are generally co-produced which must be selectively hydrogenated to a butene, but not a butane.

The so-called pygas which is a fluid stream containing hydrocarbons having 5 or more carbon atoms per molecule comprises debutanized aromatic concentrate (hereinafter referred to as DAC). Pygas or DAC therefore comprises a large variety of, for example, pentynes, pentadiene, pentatrienes, hexynes, hexadienes, hexatrienes, aromatic compounds such as, for example, benzene, toluene, xylenes, styrene, and ethylbenzene. In other words, pygas or DAC comprises a mixture of highly unsaturated $C_5+$ hydrocarbons, i.e., hydrocarbons containing 5 or more carbon atoms per molecule. Generally, the trienes are hydrogenated to dienes (diolefins) which in turn are selectively hydrogenated to monoolefins, but not to alkanes. For an aromatic compound, such as styrene which is hydrogenated to ethylbenzene, the aromatic ring is not affected by the selective hydrogenation.

In all cases, the highly unsaturated hydrocarbons described above are undesirable because they are high reactive and tend to polymerize thereby forming gums if they are left in the product stream which is used for gasoline or for further processing. As such, they must be removed. A preferred process for removing the highly unsaturated hydrocarbons is a selective hydrogenation which is defined hereinbelow.

The selective hydrogenation of a highly unsaturated hydrocarbon is generally, commercially carried out in the presence of an alumina-supported palladium catalyst. In the case of the selective hydrogenation of acetylene to ethylene, a palladium-containing catalyst supported on an alumina in which palladium is optionally distributed on the skin of the aluminum support can be employed. See for example U.S. Pat. No. 4,404,124 and U.S. Pat. No. 4,484,015, disclosures of which are herein incorporated by reference. The operating temperature for this hydrogenation process is selected such that essentially all highly unsaturated hydrocarbon, such as, for example, acetylene is hydrogenated to its corresponding alkene such as, for example, ethylene thereby removing the alkyne from the product stream while only an insignificant amount of alkene is hydrogenated to alkane. Such a selective hydrogenation process can minimize the losses of desired unsaturated hydrocarbons and, in the front-end and total cracked gas processes, avoids a "runaway" reaction which is difficult to control, as has been pointed out in the above-identified patents.

It is generally known to those skilled in the art that impurities such as carbon monoxide, $H_2S$, COS, mercaptans, organic sulfides, thiophenes, or derivatives thereof which are present in a product stream such as, for example, pygas can poison and deactivate a palladium-containing catalyst. For example, carbon monoxide is well known to temporarily poison and deactivate a hydrogenation catalyst. There is therefore an ever-increasing need to develop a catalyst which is suitable for selective hydrogenation of a highly unsaturated hydrocarbon such as, for example, a diolefin in a pygas, especially in the presence of an impurity, to a monoolefin.

Palladium supported on alumina has been successfully used in dry hydrogenation processes for many years. However, in some processes such as the so-called "total cracked gas" process in which the steam is not removed from the olefins stream, the selective hydrogenation of an alkyne to alkene must be accomplished in the presence of steam. In such processes, the alumina supported catalyst may have a much shorter life because alumina is not stable in steam. Therefore, there is also an increasing need to develop a palladium catalyst on a steam-stable support.

As such, development of an improved palladium catalyst and a process therewith in the selective hydrogenation of a highly unsaturated hydrocarbon such as a diolefin to a monoolefin in the presence of an impurity would be a significant contribution to the art and to the economy.

SUMMARY OF THE INVENTION

It is an object of this invention to provide a composition that can be used for selectively hydrogenating a highly unsaturated hydrocarbon such as a diolefin to a monoolefin. It is another object of this invention to provide a palladium-containing catalyst composition having incorporated therein a selectivity enhancer. It is also an object of this invention to provide a process for selectively hydrogenating a diolefin to its corresponding monoolefin. It is a further object of this invention to carry out a selective hydrogenation of a highly unsaturated hydrocarbon in a pygas to a monoolefin. Other objects and advantages will become more apparent as this invention is more fully described hereinbelow.

According to a first embodiment of this invention, a composition which can be used for selectively hydrogenating a highly unsaturated hydrocarbon such as, for example, a diolefin, is provided. The composition comprises palladium, at least one selectivity enhancer, and an inorganic support. The composition can also comprise silver.

According to a second embodiment of this invention, a process which can be used for selectively hydrogenating a highly unsaturated hydrocarbon to a less unsaturated hydrocarbon is provided. The process comprises contacting a highly unsaturated hydrocarbon with hydrogen, in the presence of a catalyst composition, under a condition sufficient to effect a selective hydrogenation of the highly unsaturated hydrocarbon. The catalyst composition can be the same as the composition disclosed in the first embodiment of this invention.

DETAILED DESCRIPTION OF THE INVENTION

As used in the present invention, the term "fluid" denotes gas, liquid, or combination thereof. The term "saturated hydrocarbon" is referred to as any hydrocarbon which can be converted to an unsaturated hydrocarbon such as an olefinic compound by a thermal cracking process. An "unsaturated hydrocarbon" as used in this application is a hydrocarbon having at least one double bond between carbon atoms in the molecule. Generally, examples of saturated hydrocarbons include, but are not limited to, ethane, propane, butanes, pentanes, hexanes, octanes, decanes, naphtha, and combinations of any two or more thereof. Examples of unsaturated hydrocarbons include, but are not limited to, monoolefins such as ethylene, propylene, butenes, pentenes, cyclopentene, hexenes, cyclohexene, octenes, and decenes; aromatic compounds such as naphthalene; alkynes such as acetylene, propyne, and butynes; diolefins such as propadiene, butadienes, pentadienes (including isoprene), hexadienes, octadienes, decadiene, cyclobutadiene, cyclopentadiene, cyclohexadiene, cyclooctadiene, and cyclodecadiene; and combinations of two or more thereof. The term "highly unsaturated hydrocarbon" refers to a hydrocarbon which contains a triple bond or two or more double bonds in a molecule. The term "less unsaturated hydrocarbon" refer to a hydrocarbon in which the triple bond in the highly unsaturated hydrocarbon is hydrogenated to a double bond or to a hydrocarbon in which the number of double bonds is at least one less than that in the highly unsaturated hydrocarbon, preferably the less unsaturated hydrocarbon is a monoolefin. The term "selective hydrogenation" is referred to as a hydrogenation process which converts a highly unsaturated hydrocarbon such as an alkyne, a diolefin, or a triene, to a less unsaturated hydrocarbon such as a monoolefin without hydrogenating the less unsaturated hydrocarbon to a saturated or a more saturated hydrocarbon such as alkane. Generally, an aromatic ring remains unchanged in a selective hydrogenation. For example, styrene is hydrogenated to ethylbenzene.

According to the first embodiment of this invention, a composition which can be used to selectively hydrogenate a highly unsaturated hydrocarbon to a less unsaturated hydrocarbon is provided. The composition can comprise, consist essentially of, or consists of palladium, a selectivity enhancer, and an inorganic support wherein the selectivity enhancer is selected from the group consisting of lead, bismuth, thorium, iridium, tin, antimony, gallium, germanium, arsenic, cadmium, mercury, and combinations of any two or more thereof, the inorganic support can be an inorganic oxide, and a spinel, or combinations of two or more thereof; and the inorganic oxide can be a clay, an alumina, a silica, or combinations of any two or more thereof. If a spinel support is used, the metal of the spinel is selected from the group consisting of zinc, magnesium, iron, manganese, any metal that can form a spinel structure, such as Zr, Mo, Ru, Rh, Co, Ge, Ca, and combinations of any two or more thereof. The palladium can be distributed throughout the support or present on the skin of the composition and the selectivity enhancer also can be distributed on the skin of or throughout the composition. The composition can also comprise silver. The presently preferred inorganic oxide is an alumina. The presently preferred spinel is zinc aluminate, zinc titanate, magnesium aluminate, or combinations of any two or more thereof. These spinels are readily available and effective. The term "skin" is referred to as the surface of the composition. The "skin" can be any thickness as long as such thickness can promote the selective hydrogenation disclosed herein. Generally, the thickness of the skin can be in the range of from about 1 to about 1000, preferably about 5 to about 750, more preferably about 5 to about 500, and most preferably 10 to 3000 $\mu$m. Presently, it is preferred that palladium and a selectivity enhancer are supported on an inorganic oxide support.

Generally, palladium can be present in the composition in any weight percent (%) so long as the weight % is effective to selectively hydrogenate an alkyne to an alkene, or a diolefin to a monoolefin. The weight % of palladium can be in the range of from about 0.0001 to about 5, preferably about 0.0005 to about 3, and most preferably 0.001 to 1.5%. Similarly, the selectivity enhancer can be present in the composition in any weight % as long as the weight % can improve the selectivity of a selective hydrogenation of an alkyne to an alkene, or a diolefin to a monoolefin as compared to the use of a catalyst containing palladium and an inorganic support. Generally, a selectivity enhancer can be present in the composition in the range of from about 0.0003 to about 20, preferably about 0.001 to about 10, and most preferably 0.003 to 5 weight %. Silver, if present, can be in the same weight % as the selectivity enhancer.

Optionally, the composition can also comprise, consist essentially of, or consist of palladium, a selectivity enhancer, an alkali metal or alkali metal-containing compound, and an inorganic support disclosed above. The alkali metal or alkali metal-containing compound can be present in the composition in any weight % that can effect the selective hydrogenation of a highly unsaturated hydrocarbon to a less unsaturated hydrocarbon, and in the range of from about 0.0001 to about 10, preferably about 0.001 to about 5, and most preferably about 0.005 to about 3 weight %. The presently preferred alkali metal compound is an alkali metal fluoride such as, for example, potassium fluoride.

Generally, the inorganic support can make up the rest of the composition.

The composition can be in any physical form and dimension so long as the physical form and dimension can be used as a catalyst for selectively hydrogenating an alkyne to an alkene, or a diolefin to a monoolefin. Generally, it is preferred the physical form be spherical or cylindrical for such form is easy to handle. The composition can generally have a size in the range of from about 0.1 to about 20, preferably about 0.5 to about 15, and most preferably 1 to 10 mm in diameter. The composition can have a surface area of from about 0.1 to about 150, preferably about 0.5 to about 50 m$^2$/g, as determined by the well-known BET method employing nitrogen.

According to the invention, any inorganic oxide can be used as a support for the composition so long as the inorganic oxide can effect the selective hydrogenation of a highly unsaturated hydrocarbon to a less unsaturated hydrocarbon. Examples of suitable inorganic oxide include, but are not limited to, an alumina, a silica, a clay, or combinations thereof.

Generally, any spinel can be used as the support in the composition so long as the composition can effect the selective hydrogenation of an alkyne to an alkene, or a diolefin to a monoolefin. As disclosed above, the metal of the spinel can include magnesium, zinc, iron, manganese, any metal that can form a spinel, and combinations of any two or more thereof. Examples of suitable spinels include, but are not limited to, zinc aluminate, magnesium aluminate, zinc titanate, calcium aluminate, manganese aluminate, ferrous aluminate, calcium titanate, magnesium titanate, and combinations of any two or more thereof.

The composition can be prepared by any suitable techniques. Generally, the palladium can be placed on an inorganic support in any suitable manner that will yield a composition meeting the above-described parameters. The presently preferred technique involves impregnating an inorganic support with an aqueous solution of a suitable palladium compound. Generally, the extent of penetration of the palladium can be controlled by adjustment of the acidity of the solution with an acid such as, for example, hydrochloric acid.

Examples of suitable palladium compounds include, but are not limited to, palladium chloride, palladium bromide, palladium iodide, palladium acetate, palladium nitrate, palladium sulfate, palladium sulfide, palladium acetylacetonate, and combinations of any two or more thereof. The presently preferred palladium compound is palladium chloride for it is readily available.

One can use any suitable method to determine whether the composition particles have the palladium concentrated in an area within certain distance of the exterior surface. One technique currently favored is the electron microprobe which is well known to one skilled in the art. Another technique involves breaking open a representative sample of calcined catalyst pills and treating them with a dilute alcoholic solution of N,N-dimethyl-para-nitrosoaniline. The treating solution reacts with the oxidized palladium to give a red color which can be used to evaluate the distribution of the palladium. Still another technique involves breaking open a representative sample of calcined catalyst pills followed by treatment with a reducing agent such as, for example, hydrogen to change the color of the skin.

The selectivity enhancer can be distributed on the skin of or throughout the composition in any suitable and effective manner such as the process disclosed above for incorporating palladium into or impregnating palladium onto a support. Examples of suitable selectivity enhancer compounds include, but are not limited to, lead chloride, lead bromide, lead iodide, lead acetate, lead nitrate, lead sulfate, lead fluoride, lead perchloride, bismuth chloride, bismuth bromide, bismuth iodide, bismuth acetate, bismuth nitrate, bismuth sulfate, bismuth fluoride, bismuth perchloride, gallium chloride, gallium bromide, gallium iodide, gallium acetate, gallium nitrate, gallium sulfate, gallium fluoride, gallium perchloride, thorium chloride, thorium bromide, thorium iodide, thorium acetate, thorium nitrate, thorium sulfate, thorium fluoride, thorium perchloride, iridium chloride, iridium bromide, iridium iodide, iridium acetate, iridium nitrate, iridium sulfate, iridium fluoride, iridium perchloride, tin chloride, tin bromide, tin iodide, tin acetate, tin nitrate, tin sulfate, tin fluoride, tin perchloride, antimony chloride, antimony bromide, antimony iodide, antimony acetate, antimony nitrate, antimony sulfate, antimony fluoride, antimony perchloride, germanium chloride, germanium bromide, germanium iodide, germanium acetate, germanium nitrate, germanium sulfate, germanium fluoride, germanium perchloride, arsenic chloride, arsenic bromide, arsenic iodide, arsenic acetate, arsenic nitrate, arsenic sulfate, arsenic fluoride, arsenic perchloride, cadmium chloride, cadmium bromide, cadmium iodide, cadmium acetate, cadmium nitrate, cadmium sulfate, cadmium fluoride, cadmium perchloride, mercury chloride, mercury bromide, mercury iodide, mercury acetate, mercury nitrate, mercury sulfate, mercury fluoride, mercury perchloride, and combinations of any two or more thereof. It is currently preferred to employ an aqueous nitrate solution of one of these compounds in a quantity greater than that necessary to fill the pore volume of the support. Generally, the weight ratio of selectivity enhancer compound to palladium compound can be such that the weight ratio of selectivity enhancer to palladium is in the range of from about 0.1:1 to about 20:1, and preferably about 1:1 to about 10:1.

Silver can also be used as an additional selectivity enhancer. Examples of suitable silver compounds include, but are not limited to, silver chloride, silver bromide, silver iodide, silver acetate, silver nitrate, silver sulfate, silver fluoride, silver perchloride, and combinations of any two or more thereof. The weight ratio of silver compound to palladium compound can be the same as that disclosed above for selectivity enhancer compound to palladium compound.

Thereafter, the impregnated composition can be dried at a temperature in the range of about 25° C. to about 150° C., preferably about 25° C. to 120° C., and most preferably 30° C. to 120° C., followed by calcining at a temperature of from about 200° C. to about 1,200° C., preferably about 275° C. to about 850° C., and most preferably 400° C. to 700° C. for about 1 to about 40 hours, preferably about 1 to about 30 hours, and most preferably 2 to 25 hours.

Any alkali metal or alkali metal-containing compounds can be used in the composition, with or without silver presence, if the resulting composition can effect a selective hydrogenation of a highly unsaturated hydrocarbon to a less unsaturated hydrocarbon. Examples of suitable alkali metal compounds include sodium fluoride, potassium fluoride, lithium fluoride, rubidium fluoride, cesium fluoride, sodium iodide, potassium iodide, lithium iodide, rubidium iodide, cesium iodide, sodium chloride, potassium chloride, lithium chloride, rubidium chloride, cesium chloride, sodium bromide, potassium bromide, lithium bromide, rubidium bromide, cesium bromide, sodium hydroxide, potassium hydroxide, lithium hydroxide, rubidium hydroxide, cesium hydroxide, sodium oxide, potassium oxide, lithium oxide, rubidium oxide, cesium oxide, sodium carbonate, potassium carbonate, lithium carbonate, rubidium carbonate, cesium carbonate, sodium nitrate, potassium nitrate, lithium nitrate, rubidium nitrate, cesium nitrate, and combinations of any two or more thereof. The presently preferred alkali metal-containing compound is potassium fluoride for it is effective in the selective hydrogenation. The alkali metal-containing compound can be incorporated into a support by any methods known to one skilled in the art. For example, an alkali metal-containing compound can be impregnated or sprayed onto a support before the support is impregnated with a suitable palladium compound, and preferably also with a suitable selectivity enhancer compound. Alternatively, the alkali metal-containing compound can be incorporated, for example, by impregnation or spraying onto the composition simultaneously with or after the impregnation with a suitable palladium compound. The alkali metal-containing compound can also be incorporated into a support between the palladium and selectivity enhancer impregnation steps or after the impregnation with palladium and selectivity enhancer compounds. Alternatively, one can also apply a "wet reducing" step which is a treatment with dissolved reducing agents such as hydrazine, alkali metal borohydrides, aldehydes such as formaldehyde, carboxylic acids such as formic acid or ascorbic acid, reducing sugars such as dextrose.

In the second embodiment of this invention, a process for selectively hydrogenating a highly unsaturated hydrocarbon such as, for example, an alkyne or a diolefin, to a less unsaturated hydrocarbon such as, for example, a monoolefin is provided. The process can comprise, consist essentially of, or consist of contacting a fluid feed comprising a highly unsaturated hydrocarbon with hydrogen, in the presence of a catalyst under a condition sufficient to effect the selective hydrogenation of an alkyne to an alkene, or a diolefin to a monoolefin. Though any highly unsaturated hydrocarbon can be used in the process, it is presently preferred that an alkyne, a diolefin, or a triene containing 2 to about 15, preferably 2 to about 12, and most preferably 2 to 10 carbon atoms be used.

The catalyst composition can be the same composition described above in the first embodiment of this invention. Hydrogen can be present either in the fluid feed stream containing the highly unsaturated hydrocarbon or in a hydrogen-containing fluid which is mixed with the fluid feed stream before contacting with the catalyst composition. If a hydrogen-containing fluid is used, it can be a substantially pure hydrogen or any fluid containing sufficient concentration of hydrogen to effect the hydrogenation. It can also contain other gases such as, for example, nitrogen, methane, carbon monoxide, carbon dioxide, steam, or combinations of any two or more thereof so long as the hydrogen-containing fluid contains sufficient concentration of hydrogen to effect the hydrogenation.

Optionally, the catalyst can be first treated, prior to the selective hydrogenation, with a reducing agent, such as a hydrogen-containing fluid, to activate the catalyst. Such reductive, or activation, treatment can be carried out at a temperature in the range of about 20° C. to about 300° C., preferably about 25° C. to about 250° C., and most preferably 30° C. to 200° C. for a time period of about 1 minute to about 30 hours, preferably about 0.5 to about 25 hours, and most preferably 1 to 20 hours. During this reductive treatment, the oxidation state of palladium and selectivity enhancer compounds can be substantially reduced, for example, to palladium metal and selectivity enhancer metal. However, alkali metal compounds generally are not reduced by this treatment. When this optional reductive treatment is not carried out, the hydrogen gas present in the reaction medium accomplishes this reduction of oxides of palladium and selectivity enhancer during the initial phase of the selective hydrogenation reaction of this invention.

The selective hydrogenation process of this invention can be carried out by contacting a fluid which comprises a highly unsaturated hydrocarbon, in the presence of hydrogen, with the catalyst composition disclosed above. The fluid comprising a highly unsaturated hydrocarbon can further comprise a fluid which can be water, steam, water containing a soluble or insoluble substance, or combinations of any two or more thereof. Preferably the fluid containing a highly unsaturated hydrocarbon is a pygas stream containing an alkyne, a diolefin, a triene, or combinations of two or more thereof or is an unsaturated alkene stream containing an alkyne, a diolefin, a triene, or combinations of two or more thereof as an impurity, generally at a level of about 1 mg/Kg (ppm) to about 50,000 ppm of the fluid. The highly unsaturated hydrocarbon can be, for example, an alkyne, a diolefin, or triene, or combinations of any two or more thereof. Examples of suitable alkynes include, but are not limited to, acetylene, propyne, 1-butyne, 2-butyne, 1-pentyne, 2-pentyne, 3methyl-1-butyne, 1-hexyne, 1-heptyne, 1-octyne, 1-nonyne, 1-decyne, and combinations of any two or more thereof. These alkynes are primarily hydrogenated to the corresponding alkenes. For example, acetylene is primarily hydrogenated to ethylene, propyne is primarily hydrogenated to propylene, the butynes are primarily hydrogenated to the corresponding butenes (1-butene, 2-butenes), and pentynes are primarily hydrogenated to pentenes. Examples of suitable diolefins include, but are not limited to, propadiene, butadienes, isoprene, pentadienes, cyclopentadienes, hexadienes, cyclohexadienes, heptadienes, octadienes, cyclooctadienes, nonodienes, decadienes, methylcyclopentadienes, cycloheptadienes, methylcyclohexadienes, dimethylcyclopentadienes, ethylcyclopentadienes, methylheptadienes, dimethylhexadienes, ethylhexadienes, trimethylpentadienes, methyloctadienes, dimethylheptadienes, ethylheptadienes, trimethylheptadienes, and combinations of any two or more thereof. These diolefins are selectively hydrogenated to their corresponding monoolefins. Examples of suitable trienes include, but are not limited to, pentatrienes, cyclopentatrienes, hexatrienes, cyclohexatrienes, heptatrienes, octatrienes, cyclooctatrienes, nonotrienes, decatrienes, methylcyclopentatrienes, cycloheptatrienes, methylcyclohexatrienes, dimethylcyclopentatrienes, ethylcyclopentatrienes, methylheptatrienes, dimethylhexatrienes, ethylhexatrienes, trimethylpentatrienes, methyloctatrienes, dimethylheptatrienes, ethylheptatrienes, trimethylheptatrienes, and combinations of any two or more thereof. In order to best attain substantially complete selective hydrogenation of a highly unsaturated hydrocarbon, there should be at least about one mole of hydrogen for each mole of the alkyne or diolefin present and two moles of hydrogen for each mole of the triene present in the fluid feed stream. A fluid containing a highly unsaturated hydrocarbon and hydrogen can be introduced into a reactor. Alternatively, a fluid containing a highly unsaturated hydrocarbon and a hydrogen-containing fluid can be introduced into a reactor separately, contemporaneously introduced, or premixed before their introduction to a reactor to contact with the catalyst which is generally laced in the reactor before introduction of the fluid(s) into the reactor. Any reactors known to one skilled in the art for selective hydrogenation can be employed in the present invention. The process of the invention can be carried out in a batch, semi-batch, or continuous mode.

The term "impurity" used herein denotes any component in a fluid stream that is not a major component. Examples of impurities other than an alkyne or a diolefin include, but are not limited to carbon monoxide, hydrogen sulfide, carbonyl sulfide (COS), mercaptans (RSH), organic sulfides (RSR), organic disulfides (RSSR), thiophenes, thiophanes, methane, ethane, propane, butane, carbon dioxide, water, alcohols, ethers, aldehydes, ketones, carboxylic acids, esters, other oxygenated compounds, and combinations of two or more thereof, wherein each R can be an alkyl or cycloalkyl or aryl group containing 1 to about 15, preferably 1 to 10 carbon atoms. Generally, each impurity is present in the fluid stream in trace amounts. For example, an impurity can be present at a level of less than about 1 weight percent (%).

The temperature necessary for the selective hydrogenation of a highly unsaturated hydrocarbon such as, for example, an alkyne, to a less unsaturated hydrocarbon such as, for example, an alkene is any temperature that can effect the conversion of, for example, an alkyne to an alkene. It generally depends largely upon the activity and selectivity of a catalyst, the amounts of impurities in the fluid, and the desired extent of removal of impurities. Generally, a reaction temperature can be in the range of about 10° C. to about 300° C., preferably about 20 to about 250° C., and most preferably 30 to 200° C. Any suitable reaction pressure can be employed. Generally, the total pressure is in the range of about 50 to about 1,500, preferably about 75 to about 1,200, and most preferably 100 to 1,000 pounds per square inch gauge (psig). The liquid or gas hourly space velocity of the fluid feed can also vary over a wide range. Typically, the gas space velocity can be in the range of about 10 to about 20,000 m$^3$ of the fluid per m$^3$ of catalyst per hour, more preferably about 50 to about 12,500 m$^3$/m$^3$/hour, and most preferably 100 to 8,000 m$^3$/m$^3$/hour. The liquid space velocity of the feed can be in the range of from about 0.001 to about 200, preferably about 0.01 to about 100, and most preferably 0.1 to 50 m$^3$/m$^3$/hour. The molar ratio of hydrogen to a highly unsaturated hydrocarbon is in the range of about 0.5:1 to about 10,000:1, preferably about 1:1 to about 5,000:1 and most preferably 1:1 to 1,000:1. The hourly space velocity of the hydrogen-containing fluid, if separately fed to a reactor containing a selective hydrogenation catalyst, is chosen so as to provide a molar ratio of H$_2$ to a highly unsaturated hydrocarbon in the range of about 0.5:1 to about 10,000:1, preferably about 1:1 to about 5,000:1 and most preferably 1:1 to 1,000:1.

Regeneration of the catalyst composition can be accomplished by heating the catalyst composition in air (at a temperature which preferably does not exceed about 700° C.) so as to burn off any impurities such as, for example, organic matter and/or char that may have accumulated on the catalyst composition. Optionally, the oxidatively regenerated composition is reduced with H$_2$ or a suitable hydrocarbon (as has been described above) before its redeployment in the selective hydrogenation of this invention.

The following examples are presented to further illustrate this invention and are not to be construed as unduly limiting the scope of the invention.

EXAMPLE I

This comparative example illustrates a selective hydrogenation using a commercially available catalyst. More specifically this example involved the selective hydrogenation of a (high diolefin) pygas stream (C$_5$+ co-product stream) from an olefin plant. The primary goal was the selective hydrogenation of C$_5$ diolefins to C$_5$ monoolefins (without making the C$_5$ alkane). The secondary goal was the conversion of styrene to ethylbenzene.

The catalyst used was Calsicat E-144SDU which was obtained from Mallinckrodt Chemical Inc., Calsicat, Erie, Pa. It was 0.5% Pd on 1/16 inch alumina spheres which had about 40 m$^2$/g surface area. The liquid feed used in the runs was obtained from Phillips Petroleum Company's olefin plants. The composition of this liquid feed was about 72 weight % BTX (about 55 weight % benzene, 15 weight % toluene, 2 weight % xylenes) with about 6 to 8 weight % styrene and 2 weight % ethylbenzene, also with about 0.1 weight % total C$_5$ alkanes (including cyclopentane), 3 weight % total C$_5$ monoolefins (including cyclopentene), 4 weight % total C$_5$ diolefins (including cyclopentadiene), and about 3 weight % dicyclopentadiene, the remaining about 8 to 10 weight % was made up of many small components, mainly C$_6$–C$_{10}$ olefins and diolefins.

A portion (20.0 cc or about 17.5 g) of catalyst was loaded into a ½ inch inner diameter stainless steel reactor equipped with a ⅛ inch center thermocouple well. The reactor was mounted in a tube furnace. While the reactor was purging with pure hydrogen gas, it was warmed to 100° F., and pressured up to 350 psig with H$_2$ gas. The catalyst was pretreated for 1 hour, at 100° F., with 100 cc/min H$_2$ flowing. The H$_2$ flow rate was controlled by a Brooks mass flow controller.

The hydrogen flow rate was then dropped to about 60 cc/min, and the liquid feed pump (Waters Associates, Inc. Model 6000A Solvent Delivery System) started at a rate of 1.0 cc/min where it was maintained throughout the run. The catalyst performance was mapped out as a function of styrene conversion. The catalyst bed hot spot temperature was maintained at about 200–205° F. throughout the run (by adding, or more often, since the reaction was highly exothermic, removing heat as necessary). The conversion was controlled by varying the H$_2$ rate in the range of about 40 to 140 cc/min as shown in Table I. The reactor was allowed to line out, or stabilize, at a given set of conditions for at least 1.5 hours before the liquid product from the reactor was sampled. The liquid product was analyzed by GC-FID using a standard boiling point type capillary column.

The catalysts selectivity was measured by the ability to single-step hydrogenate aliphatic (noncyclic) C$_5$ diolefins to aliphatic C$_5$ monoolefins (without further hydrogenating the monoolefins to aliphatic C$_5$ paraffins). First, the feed was analyzed by GC, which individually identified and quantified all the C$_5$ hydrocarbons. Then, the maximum theoretical aliphatic C$_5$ olefins for the feed was approximated as the total weight % of all aliphatic C$_5$ mono-olefins in the feed (3-methylbutene-1,1-pentene, 2-methylbutene-1, trans-pentene-2, cis-pentene-2, and 2-methylbutene-2) plus the total weight % of all aliphatic C$_5$ diolefins in the feed (1,4-pentadiene, isoprene, and 1,3-pentadiene). Secondly, the total weight % of all aliphatic C$_5$ monoolefins was found for each product sample (i.e., the sum of the 3-methylbutene-1,1-pentene, 2-methylbutene-1, trans-pentene-2, cis-pentene-2, and 2-methylbutene-2 peaks). Then the Percent of Theoretical C$_5$ Olefin Make (PTOM) was calculated as:

$$PTOM = \frac{\text{total weight \% of all aliphatic } C_5 \text{ monoolefins (for the product)} \times 100}{\text{maximum theoretical aliphatic } C_5 \text{ olefins (for the feed)}}$$

The results are shown in Table I which shows the GC results and PTOM, as a function of styrene conversion, for the catalyst of Example I. As can be seen, the conversion was controlled by variation of the hydrogen rate.

TABLE I[a]

| Sample Number | H$_2$ cc/min | Temp (° F.) | Total C$_5$ Paraffins | Total C$_5$ Olefins | Total C$_5$ Diolefins | cyC$_5$ | cyC$_5$= | cyC$_5$== | Styrene Conv. | PTOM |
|---|---|---|---|---|---|---|---|---|---|---|
| 1 (feed) | | | 0.04 | 1.58 | 2.65 | 0.03 | 1.24 | 1.18 | 0.00 | 37.3 |
| 2 | 60 | 206 | 1.83 | 2.39 | 0.58 | 0.69 | 0.80 | 0.25 | 46.00 | 56.5 |
| 3 | 70 | 211 | 1.89 | 2.65 | 0.40 | 0.78 | 0.75 | 0.17 | 57.70 | 62.6 |
| 4 | 80 | 202 | 2.61 | 2.23 | 0.13 | 1.08 | 0.50 | 0.06 | 80.70 | 52.7 |
| 5 | 90 | 208 | 3.39 | 1.68 | 0.00 | 1.42 | 0.21 | 0.00 | 96.50 | 39.6 |
| 6 (feed) | | | 0.03 | 1.62 | 2.72 | 0.03 | 1.28 | 1.21 | 0.00 | 37.2 |
| 7 | 90 | 206 | 3.29 | 1.58 | 0.05 | 1.36 | 0.23 | 0.02 | 94.80 | 36.4 |
| 8 | 85 | 202 | 3.16 | 1.85 | 0.00 | 1.39 | 0.24 | 0.00 | 96.00 | 42.6 |
| 9 | 80 | 203 | 2.96 | 1.99 | 0.05 | 1.31 | 0.29 | 0.02 | 87.40 | 45.9 |
| 10 | 75 | 207 | 2.61 | 2.25 | 0.09 | 1.18 | 0.41 | 0.04 | 87.30 | 51.8 |
| 11 | 70 | 211 | 2.37 | 2.48 | 0.14 | 1.10 | 0.48 | 0.06 | 83.30 | 57.2 |
| 12 | 65 | 205 | 4.26 | 0.70 | 0.00 | 1.60 | 0.01 | 0.00 | 99.70 | 16.1 |

[a]Total C$_5$ denotes aliphatic C$_5$'s; cyC$_5$ denotes cyclopentane; cyC$_5$= denotes cyclopentene; cyC$_5$==denotes cyclopentadiene; Temp denotes the temperature of the catalyst bed hot spot; the values for total C$_5$ paraffins, total C$_5$ olefins, total C$_5$ diolefins, CyC$_5$, OcyC$_5$=, and CyC$_5$== are weight %; and the values for styrene conversion are percent of styrene converted to ethylbenzene.

Using the data from Table I, the PTOM was plotted versus the styrene conversion. The PTOM at 95% styrene conversion was then read off the plot and the plot showed that the control catalyst gave about 43% PTOM at 95% styrene conversion.

EXAMPLE II

This example illustrates a selective hydrogenation using a Pd/alumina catalyst having incorporated thereon 0.5% lead.

Calsicat E-144SDU Pd/alumina catalyst (22.0 g) was added to a 250 ml beaker. A lead nitrate (Pb(NO$_3$)$_2$) solution prepared by dissolving 0.178 g lead nitrate with 9.3 g of bottled H$_2$O. The Pd/alumina was impregnated with the lead nitrate solution by incipient wetness method followed by drying overnight (16 hours) at 85° C. The resulting material was calcined in a programmable furnace for 2 hours at 110° C., 2 hours at 200° C., and then 4 hours at 400° C. with 200 cc/min dry air. Thereafter, the calcined catalyst was cooled to about 25° C. The selective hydrogenation using this catalyst was conducted using the same procedure described in Example I. The results are shown in Table II.

Table II shows that lead is an effective selectivity enhancer because a Pd/Pb/alumina catalyst gave a PTOM at 95% styrene conversion of 82%, when the data in Table II were plotted as described in Example I. This is better than the 43% for the Pd-only catalyst with this same feed shown in Table I.

EXAMPLE III

This example shows a selective hydrogenation of a pentadiene-rich stream using a 0.5% Pb/0.5% K (as KF) on Pd/alumina catalyst. First, 22.0 g of Calsicat E-144SDU Pd/alumina was placed in a 250 ml beaker. Thereafter a Pb/K solution containing 0.178 g of lead nitrate (Pb(NO$_3$)$_2$), 0.163 g KF, and 9.3 g of bottled H$_2$O was added by incipiently wetting the Pd/alumina with the Pb/K solution, dropwise, while stirring. The Pb/K-impregnated Pd/alumina was then dried overnight at 85° C. The dried material was calcined as described in Example II. The catalyst was used in a selective hydrogenation also as described in Example II and the results are shown in Table III.

TABLE II[a]

| Sample Number | H$_2$ cc/min | Temp (° F.) | Total C$_5$ Paraffins | Total C$_5$ Olefins | Total C$_5$ Diolefins | cyC$_5$ | cyC$_5$= | cyC$_5$== | Styrene Conv. | PTOM |
|---|---|---|---|---|---|---|---|---|---|---|
| 1 (feed) | | | 0.03 | 1.55 | 2.62 | 0.03 | 1.23 | 1.13 | 0.00 | 37.2 |
| 2 | 60 | 234 | 2.09 | 2.57 | 0.15 | 0.82 | 0.66 | 0.06 | 66.95 | 61.5 |
| 3 | 70 | 201 | 1.95 | 2.80 | 0.03 | 1.00 | 0.49 | 0.01 | 90.80 | 67.0 |
| 4 | 80 | 208 | 2.47 | 2.22 | 0.00 | 1.28 | 0.18 | 0.00 | 99.30 | 53.1 |
| 5 | 90 | 206 | 3.04 | 1.71 | 0.00 | 1.45 | 0.06 | 0.00 | 99.80 | 41.0 |
| 6 (feed) | | | 0.03 | 1.52 | 2.57 | 0.02 | 1.21 | 1.11 | 0.00 | 37.2 |
| 7 | 90 | 206 | 2.18 | 2.03 | 0.00 | 1.23 | 0.13 | 0.00 | 99.90 | 49.7 |
| 8 | 85 | 201 | 2.09 | 2.34 | 0.00 | 1.23 | 0.19 | 0.00 | 99.40 | 57.2 |
| 9 | 80 | 201 | 2.17 | 2.39 | 0.00 | 1.25 | 0.18 | 0.00 | 99.70 | 58.6 |
| 10 | 75 | 207 | 1.97 | 2.64 | 0.00 | 1.23 | 0.23 | 0.00 | 100.00 | 64.6 |
| 11 | 70 | 206 | 1.55 | 2.78 | 0.00 | 1.01 | 0.36 | 0.00 | 99.60 | 68.1 |
| 12 | 65 | 203 | 1.31 | 3.29 | 0.00 | 0.85 | 0.59 | 0.00 | 95.70 | 80.5 |
| 13 | 60 | 204 | 1.10 | 3.67 | 0.00 | 0.72 | 0.76 | 0.00 | 87.70 | 89.7 |

[a]See Table I.

TABLE III[a]

| Sample Number | $H_2$ cc/min | Temp (° F.) | Total $C_5$ Paraffins | Total $C_5$ Olefins | Total $C_5$ Diolefins | $cyC_5$ | $cyC_5=$ | $cyC_5==$ | Styrene Conv. | PTOM |
|---|---|---|---|---|---|---|---|---|---|---|
| 1 (feed) |    |    | 0.03 | 1.48 | 2.51 | 0.02 | 1.18 | 1.08 | 0.00  | 37.1 |
| 2        | 60 | 170 | 1.60 | 2.59 | 0.48 | 0.58 | 0.81 | 0.20 | 41.20 | 64.9 |
| 3        | 70 | 200 | 1.46 | 2.81 | 0.26 | 0.60 | 0.79 | 0.11 | 50.90 | 70.4 |
| 4        | 80 | 204 | 2.64 | 2.12 | 0.00 | 1.15 | 0.33 | 0.00 | 96.70 | 53.3 |
| 5        | 90 | 194 | 2.19 | 2.35 | 0.00 | 1.11 | 0.33 | 0.00 | 97.40 | 59.1 |
| 6 (feed) |    |    | 0.03 | 1.46 | 2.47 | 0.03 | 1.17 | 1.07 | 0.00  | 37.1 |
| 7        | 90 | 207 | 2.29 | 2.10 | 0.00 | 1.18 | 0.23 | 0.00 | 98.70 | 53.6 |
| 8        | 85 | 206 | 2.15 | 2.43 | 0.00 | 1.15 | 0.28 | 0.00 | 98.70 | 62.0 |
| 9        | 80 | 212 | 2.10 | 2.48 | 0.00 | 1.15 | 0.27 | 0.00 | 99.10 | 63.1 |
| 10       | 75 | 206 | 1.99 | 2.79 | 0.00 | 1.16 | 0.33 | 0.00 | 99.20 | 71.0 |
| 11       | 70 | 204 | 1.66 | 3.06 | 0.00 | 1.06 | 0.42 | 0.00 | 99.70 | 77.9 |
| 12       | 65 | 203 | 1.34 | 3.42 | 0.00 | 0.85 | 0.62 | 0.00 | 96.40 | 87.1 |
| 13       | 60 | 205 | 1.13 | 3.69 | 0.00 | 0.70 | 0.77 | 0.00 | 88.40 | 93.9 |

[a]See Table I.

The results show that Pb can be effectively co-promoted with KF. This catalyst gave 89% maximum theoretical $C_5$ olefin make (PTOM) at 95% styrene conversion when the data from Table III were plotted as described in Example I.

EXAMPLE IV

This example shows a selective hydrogenation using a 1.5% bismuth on 0.5% Pd/alumina catalyst. The catalyst was prepared by first weighing 22.0 g of Calsicat E-144SDU into a 250 ml beaker. The Pd/alumina was impregnated with a solution containing 0.382 g of bismuth nitrate (pentahydrate) and 9.5 g distilled $H_2O$ and then dried 4 hours at 85° C. The catalyst was then impregnated a second time with another 0.382 g of $BiNO_3$ dissolved with 9.5 g of $H_2O$. Thereafter the resulting Bi/Pd/alumina was dried, calcined, and then used as a catalyst in a selective hydrogenation process. The results are shown in Table IV.

Table IV shows that this Bi/Pd/alumina catalyst gave about 87% maximum theoretical aliphatic $C_5$ olefin make at 95% styrene conversion when the data in Table IV were plotted as described in Example I.

EXAMPLE V

This examples illustrates a selective hydrogenation using a gallium-promoted catalyst. First, 22.0 g of Calsicat E-144SDU, described in Example I, was placed in a 250 ml beaker and was impregnated with a solution containing 1.65 g of $Ga(NO_3)_3$ and 9.5 g of bottled $H_2O$ by the process described in Example II. The gallium-promoted Pd/alumina was then dried at 90° C. overnight followed by air calcining as described in Example II to prepare a catalyst containing about 2 weight % gallium and 0.5 weight % palladium on alumina. The catalyst was used in a selective hydrogenation as described in Example I. The results are shown in Table V.

TABLE IV[a]

| Sample Number | $H_2$ cc/min | Temp (° F.) | Total $C_5$ Paraffins | Total $C_5$ Olefins | Total $C_5$ Diolefins | $cyC_5$ | $cyC_5=$ | $cyC_5==$ | Styrene Conv. | PTOM |
|---|---|---|---|---|---|---|---|---|---|---|
| 1 (feed)  |    |     | 0.04 | 1.85 | 30.03 | 0.03 | 1.43 | 1.14   | 0.00   | 37.8 |
| 2         | 60 | 206 | 2.53 | 2.86 | 0.12  | 0.90 | 0.65 | 0.04   | 80.90  | 58.7 |
| 3         | 70 | 205 | 2.49 | 3.08 | 0.01  | 1.10 | 0.46 | t[b]   | 95.90  | 63.1 |
| 4         | 80 | 204 | 3.72 | 2.25 | 0.00  | 1.54 | 0.10 | 0.00   | 99.80  | 46.1 |
| 5         | 90 | 216 | 3.53 | 1.96 | 0.00  | 1.49 | 0.07 | 0.00   | 100.00 | 40.2 |
| 6 (feed)  |    |     | 0.03 | 1.68 | 2.82  | 0.03 | 1.36 | 1.08   | 0.00   | 37.4 |
| 7         | 90 | 202 | 3.10 | 2.38 | 0.00  | 1.46 | 0.11 | 0.00   | 99.90  | 52.9 |
| 8         | 85 | 203 | 3.16 | 2.46 | 0.00  | 1.49 | 0.11 | 0.00   | 100.00 | 54.6 |
| 9         | 80 | 206 | 3.36 | 2.60 | 0.00  | 1.56 | 0.09 | 0.00   | 100.00 | 57.8 |
| 10        | 75 | 205 | 2.76 | 2.80 | 0.00  | 1.42 | 0.15 | 0.00   | 100.00 | 62.3 |
| 11        | 70 | 207 | 2.24 | 2.31 | 0.00  | 1.24 | 0.32 | 0.00   | 99.80  | 51.4 |
| 12        | 65 | 203 | 1.87 | 3.75 | 0.00  | 1.07 | 0.51 | 0.00   | 98.00  | 83.2 |
| 13 (feed) |    |     | 0.04 | 1.74 | 2.85  | 0.03 | 1.37 | 1.08   | 0.00   | 37.9 |
| 14        | 70 | 210 | 2.65 | 2.96 | 0.00  | 1.39 | 0.20 | 0000   | 99.30  | 64.5 |
| 15        | 65 | 204 | 1.89 | 3.70 | 0.00  | 1.08 | 0.49 | 0.00   | 99.10  | 80.7 |
| 16        | 60 | 203 | 1.41 | 3.99 | 0.04  | 0.86 | 0.68 | 0.01   | 94.20  | 87.0 |
| 17        | 55 | 205 | 1.27 | 4.22 | 0.12  | 0.76 | 0.80 | 0.04   | 85.80  | 92.1 |

[a]See Table I.
[b]t denotes trace amount detected.

TABLE V[a]

| Sample Number | $H_2$ cc/min | Temp (° F.) | Total $C_5$ Paraffins | Total $C_5$ Olefins | Total $C_5$ Diolefins | $cyC_5$ | $cyC_5=$ | $cyC_5==$ | Styrene Conv. | PTOM |
|---|---|---|---|---|---|---|---|---|---|---|
| 1 (feed) |  |  | 0.04 | 1.77 | 2.82 | 0.03 | 1.38 | 1.05 | 0.00 | 38.6 |
| 2 | 60 | 204 | 2.36 | 2.29 | 0.27 | 0.87 | 0.56 | 0.10 | 70.10 | 50.0 |
| 3 | 70 | 208 | 2.39 | 2.86 | 0.03 | 1.18 | 0.33 | 0.01 | 93.80 | 62.3 |
| 4 | 80 | 204 | 3.26 | 2.12 | 0.00 | 1.40 | 0.13 | 0.00 | 99.00 | 46.3 |
| 5 | 90 | 206 | 3.90 | 1.16 | 0.00 | 1.45 | 0.02 | 0.00 | 99.80 | 25.3 |
| 6 (feed) |  |  | 0.04 | 1.70 | 2.71 | 0.03 | 1.34 | 1.01 | 0.00 | 38.6 |
| 7 | 90 | 225 | 4.27 | 0.97 | 0.00 | 1.50 | 0.02 | t[b] | 99.40 | 21.9 |
| 8 | 85 | 206 | 3.82 | 1.56 | 0.00 | 1.52 | 0.01 | 0.00 | 100.00 | 35.3 |
| 9 | 80 | 207 | 3.41 | 1.80 | 0.00 | 146 | 0.04 | 0.00 | 100.00 | 40.9 |
| 10 | 75 | 201 | 2.59 | 2.61 | 0.00 | 1.37 | 0.13 | 0.00 | 100.00 | 59.2 |
| 11 | 70 | 211 | 2.35 | 3.11 | 0.00 | 1.27 | 0.28 | 0.00 | 98.10 | 70.5 |
| 12 | 65 | 206 | 1.80 | 3.29 | 0.03 | 1.07 | 0.39 | 0.01 | 93.20 | 74.5 |
| 13 | 60 | 210 | 1.54 | 3.64 | 0.06 | 0.96 | 0.54 | 0.02 | 88.20 | 82.6 |

[a]See Table I.
[b]See Table IV.

Table V shows that this catalyst gave 74% maximum theoretical aliphatic olefin ($C_5$) make at 95% styrene conversion when the data were plotted as described in Example I.

EXAMPLE VI

This example shows a selective hydrogenation of a pentadiene-rich stream using a Pd/alumina catalyst having impregnated thereon lead and silver. The catalyst was prepared by placing 22.0 g of a 0.5% Pd/1.5% Ag/alumina, which was prepared according to the method disclosed in U.S. Pat. No. 5,489,565 disclosure of which is incorporated herein by reference, into a 250 ml beaker. Thereafter, the Pd/Ag/alumina catalyst was impregnated with a solution containing 0.178 g of lead nitrate ($Pb(NO_3)_2$) dissolved with 9.0 g of bottled $H_2O$ by incipient wetness method. The lead nitrated-impregnated Pd/alumina was dried overnight at 85° C. The dried material was then calcined in a programmable furnace for 2 hours at 110° C., 2 hours at 200° C. and then 4 hours at 400° C. with 200 cc/min dry air. The catalyst was then used in a selective hydrogenation process as described in Example I. The results are shown in Table VI.

TABLE VI[a]

| Sample Number | $H_2$ cc/min | Temp (° F.) | Total $C_5$ Paraffins | Total $C_5$ Olefins | Total $C_5$ Diolefins | $cyC_5$ | $cyC_5=$ | $cyC_5==$ | Styrene Conv. | PTOM |
|---|---|---|---|---|---|---|---|---|---|---|
| 1 (feed) |  |  | 0.03 | 1.55 | 2.62 | 0.03 | 1.24 | 1.14 | 0.00 | 37.2 |
| 2 | 60 | 173 | 1.43 | 2.82 | 0.37 | 0.60 | 0.84 | 0.16 | 47.10 | 67.5 |
| 3 | 70 | 203 | 1.21 | 3.10 | 0.24 | 0.56 | 0.87 | 0.10 | 57.50 | 74.3 |
| 4 | 80 | 205 | 1.19 | 3.29 | 0.12 | 0.63 | 0.84 | 0.04 | 75.95 | 78.9 |
| 5 | 90 | 198 | 1.22 | 3.21 | 0.10 | 0.68 | 0.80 | 0.04 | 79.20 | 77.0 |
| 6 | 100 | 199 | 1.11 | 3.15 | 0.10 | 0.65 | 0.79 | 0.04 | 78.40 | 75.6 |
| 7 (feed) |  |  | 0.03 | 1.58 | 2.66 | 0.03 | 1.26 | 1.15 | 0.00 | 37.3 |
| 8 | 90 | 225 | 1.26 | 3.20 | 0.05 | 0.81 | 0.67 | 0.01 | 89.60 | 75.4 |
| 9 | 85 | 199 | 0.85 | 3.37 | 0.09 | 0.58 | 0.84 | 0.03 | 78.20 | 79.5 |
| 10 | 80 | 207 | 1.02 | 3.42 | 0.05 | 0.69 | 0.76 | 0.01 | 86.90 | 80.6 |
| 11 | 75 | 211 | 1.08 | 3.80 | 0.04 | 0.71 | 0.84 | 0.01 | 88.00 | 89.6 |
| 12 | 70 | 208 | 0.92 | 3.46 | 0.04 | 0.63 | 0.79 | 0.01 | 86.60 | 81.5 |
| 13 | 70 | 230 | 1.05 | 37.3 | 0.03 | 0.71 | 0.80 | 0.01 | 89.90 | 87.8 |
| 14 | 65 | 230 | 1.01 | 3.75 | 0.03 | 0.68 | 0.81 | 0.01 | 90.10 | 88.4 |
| 15 (feed) |  |  | 0.03 | 1.50 | 2.52 | 0.03 | 1.21 | 1.10 | 0.00 | 37.3 |
| 16 | 65 | 241 | 0.96 | 3.64 | 0.04 | 0.69 | 0.78 | 0.01 | 91.80 | 90.5 |
| 17 | 60 | 233 | 0.94 | 3.91 | 0.00 | 0.67 | 0.85 | 0.00 | 96.50 | 97.3 |
| 18 | 55 | 216 | 0.70 | 4.04 | 0.03 | 0.47 | 1.02 | 0.01 | 91.60 | 100.4 |
| 19 | 55 | 225 | 0.71 | 4.12 | 0.03 | 0.48 | 1.03 | 0.01 | 91.50 | 102.5 |
| 20 | 50 | 230 | 0.55 | 4.22 | 0.09 | 0.37 | 1.12 | 0.02 | 80.60 | 105.1 |

[a]See Table I.

When the data shown in Table VI were plotted as described in Example I, the plot showed that this catalyst gave 98% maximal theoretical aliphatic $C_5$ olefin make (PTOM) at 95% styrene conversion. This 98% PTOM is much better than the 43% for a commercial catalyst shown in Example I.

The results shown in the above tables also clearly demonstrate that the catalysts of this invention are highly effective for the complete removal of both aliphatic and cyclic diolefins from the feed because little or no diolefins were observed in the reactor effluent.

The selectivity (or the PTOM), as shown above, was a function of conversion. That is, for a given catalyst, the PTOM (selectivity) would vary depending on the severity of the reaction conditions (temperature, pressure, hydrogen rate, etc.). Therefore, for the direct comparison of one catalyst to a second catalyst to be meaningful, they must be compared under conditions of constant conversion. The constant conversion condition was chosen to be the point of 95% conversion of styrene to ethylbenzene. Therefore, the measure of selectivity reported for each catalyst was the PTOM at 95% styrene conversion. The PTOM's at 95% styrene conversion described in Tables I–VI are summarized below in Table VII.

TABLE VII

| Catalyst | PTOM[a] |
|---|---|
| control (0.5% Pd/Al$_2$O$_3$) | 43 (I) |
| 0.5% Pb/0.5% Pd/Al$_2$O$_3$ | 82 (II) |
| 0.5% Pb/0.5% KF/0.5% Pd/Al$_2$O$_3$ | 89 (III) |
| 1.5% Bi/0.5% Pd/Al$_2$O$_3$ | 87 (IV) |
| 2% Ga/0.5% Pd/Al$_2$O$_3$ | 74 (V) |
| 0.5% Pb/1.5% Ag/0.5% Pd/Al$_2$O$_3$ | 98 (VI) |

[a]The Roman numeral in the parenthesis corresponds to Example numeral.

Table VII clearly demonstrates that the selectivity enhancers of the invention significantly increased the effectiveness of the catalysts containing the selectivity enhancers as compared to the control catalyst. Table VII also demonstrates that silver, a commonly used selectivity enhancer, can be combined with the selectivity enhancers of the present invention to further increase the effectiveness of the catalysts containing the selectivity enhancers as compared to the control catalyst. Table VII further demonstrates the effectiveness of an alkali metal halide on improving the selectivity of a selective dehydrogenation catalyst having incorporated therein a selectivity enhancer of the present invention.

The results shown in the above examples also clearly demonstrate that the present invention is well adapted to carry out the objects and attain the ends and advantages mentioned as well as those inherent therein. While modifications may be made by those skilled in the art, such modifications are encompassed within the spirit of the present invention as defined by the specification and the claims.

That which is claimed:

1. A composition consisting essentially of palladium, lead and alumina; the weight % of said palladium in said composition is in the range of from about 0.001 to about 1.5%; and the weight ratio of lead to palladium is in the range of about 1:1 to about 10:1; and further wherein said palladium is present as skin distributed on the surface of said alumina and the thickness of said skin is in the range of from about 1 to about 1000 μm.

2. A composition consisting essentially of palladium, a selectivity enhancer and alumina wherein said selectivity enhancer consists essentially of lead and silver and either an alkali metal or an alkali metal halide; the weight % of said palladium in said composition is in the range of from about 0.001 to about 1.5%; and the weight ratio of selectivity enhancer to palladium is in the range of about 1:1 to about 10:1; and further wherein said palladium is present as skin distributed on the surface of said alumina and the thickness of said skin is in the range of from about 1 to about 1000 μm.

3. A composition consisting essentially of palladium, a selectivity enhancer, and an inorganic support wherein said palladium and selectivity enhancer are each present in a sufficient amount to effect a selective hydrogenation of a highly unsaturated hydrocarbon to a less saturated hydrocarbon, said selectivity enhancer consists essentially of lead and silver and either an alkali metal or an alkali metal halide; and said support is selected from the group consisting of silica, alumina, spinel, and combinations of any two or more thereof wherein the weight % of said palladium in said composition is in a range of from about 0.001 to about 1.5%; and the weight ratio of selectivity enhancer to palladium is in the range of from about 1:1 to about 10:1.

4. A composition according to claim 3 wherein said palladium is present as skin distributed on the surface of said inorganic support and the thickness of said skin is in the range of from about 1 to about 1000 μm.

5. A composition according to claim 3 wherein said support is alumina.

6. A composition according to claim 2 wherein said support is alumina.

7. A composition consisting essentially of palladium, a selectivity enhancer, and an inorganic support wherein said palladium and selectivity enhancer are each present in a sufficient amount to effect a selective hydrogenation of a highly unsaturated hydrocarbon to a less saturated hydrocarbon, said selectivity enhancer consists essentially of lead and either an alkali metal or an alkali metal halide; and said support is selected from the group consisting of silica, alumina, spinel, and combinations of any two or more thereof wherein said palladium is present as skin distributed on the surface of said support and the thickness of said skin is in the range of from about 1 to about 1000 μm and wherein the weight % of said palladium in said composition is in a range of from about 0.001 to about 1.5%; and the weight ratio of selectivity enhancer to palladium is in the range of from about 1:1 to about 10:1.

8. A composition according to claim 7 wherein said support is alumina.

9. A composition consisting essentially of palladium, lead and an inorganic support wherein said palladium and lead are each present in a sufficient amount to effect a selective hydrogenation of a highly unsaturated hydrocarbon to a less saturated hydrocarbon, and said support is selected from the group consisting of silica, alumina, spinel, and combinations of any two or more thereof and said support is selected from the group consisting of silica, alumina, spinel, and combinations of any two or more thereof wherein said palladium is present as skin distributed on the surface of said alumina and the thickness of said skin is in the range of from about 1 to about 1000 μm.

10. A composition according to claim 9 wherein the weight % of said palladium in said composition is in a range of from about 0.001 to about 1.5%; and the weight ratio of selectivity enhancer to palladium is in the range of from about 1:1 to about 10:1.

11. A composition according to claim 9 wherein said support is alumina.

12. A composition according to claim 10 wherein said support is alumina.

* * * * *